United States Patent [19]

DeLuca et al.

[11] Patent Number: 5,260,199
[45] Date of Patent: Nov. 9, 1993

[54] METHOD OF PRODUCING 1,25-DIHYDROXYVITAMIN $D_3$ RECEPTOR PROTEIN

[75] Inventors: Hector F. DeLuca, Deerfield; Troy K. Ross; Jean M. Prahl, both of Madison, all of Wis.

[73] Assignee: Wisconsin Alumni Research Foundation, Madison, Wis.

[21] Appl. No.: 737,736

[22] Filed: Jul. 30, 1991

[51] Int. Cl.$^5$ ............................................. C12N 15/67
[52] U.S. Cl. ................. 435/69.1; 435/252.3; 435/320.1
[58] Field of Search ............... 435/6, 69.1, 70.1, 71.1, 435/172.1, 172.3, 252.3, 320.1; 935/9, 10

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |

OTHER PUBLICATIONS

MacDonald et al., Baculovirus-Mediated Expression of the Human Vitamin D Receptor, Oct. 5, 1991, J. Biol. Chem., 266:18808-18813.
Saini et al., Molecular events regulating messenger RNA stability in Eukaryotes, (Nov. 30, 1989), 1990, Molec. and Cellular Biochem., 96:15-23.
DNA, vol. 2, 265-273, Apr. 1983, Nishi et al., Construction and Application of a Novel Plasmid "ATG Vector" for Direct Expression of Foreign Genes in . . . .
Casey et al., Iron-Responsive Elements . . . , 1988, Science, 240:924-928.
Yen et al., Autoregulated Changes . . . , 1988, Molec. and Cell. Biochem., 8(3):1224-1235.
Mullner et al., A Stem-Loop in the . . . , 1988, Cell, 53:815-825.
Treisman, R., Transient Accumulation . . . , Cell, 42:889-902.
Fort et al., Regulation of c-fos gene . . . , 1987, NAR, 15(14), 5657-5667.
McDonnell, D. P. et al., "Molecular Cloning of Complementary RNA Encoding the Avian Receptor for Vitamin D", Science, 235:1214-1217 (1987).
Burmester, J. K. et al., "Isolation and Expression of Rat 1,25-Dihydroxyvitamin $D_3$ Receptor cDNA", Proc. Natl. Acad. Sci. USA, 85:1005-1009 (1988).
Baker, A. R. et al., "Cloning and Expression of Full-length cDNA Encoding Human Vitamin D Receptor", Proc. Natl. Acad. Sci. USA, 85:3294-3298 (1988).
McDonnell, D. P. et al., "Functional Domains of the Human Vitamin $D_3$ Receptor Regulate Osteocalcin Gene Expression", Molec. Endocrin., 3[4]:635-644 (1989).
Burmester, J. K. et al., "Structure and Regulation of the Rat 1,25-Dihydroxyvitamin $D_3$ Receptor", Proc. Natl. Acad. Sci. USA, 85:9499-9502 (1988).
Sone, T. et al., "Expression of Human Vitamin D Receptor in Saccharomyces cerevisiae", J. Biol. Chem., 265[35]:21997-22003 (1990).
Luckow, V. A., "Cloning and Expression of Heterologous Genes in Insect Cells with Baculovirus Vectors", in Recombinant DNA Technology and Applications, p. 8, McGraw-Hill, (1990).
Granados, R. R. et al., "In Vivo Infection and Replication of Baculoviruses", in The Biology of Baculoviruses I:89-108 (1986).
Summers, M. D. et al., A Manual of Methods for Baculovirus Vectors and Insect Cell Culture Procedures, pp. 6-7, Texas Agricultural Experiment Station Bulletin No. 1555 (1988).

(List continued on next page.)

Primary Examiner—Robert J. Hill, Jr.
Assistant Examiner—John P. Ulm
Attorney, Agent, or Firm—Quarles & Brady

[57] ABSTRACT

A method of producing 1,25-dihydroxyvitamin $D_3$ receptor protein is disclosed. A DNA sequence is transcribed to form an RNA sequence which encodes animal vitamin D receptor. Receptor protein is expressed from the RNA sequence. The RNA sequence contains less than the full 5' and 3' non-translated flanking sequences present in the natural form of the RNA sequence. Receptor protein produced by the above method, expression systems used in the method, and plasmids useful in constructing such expression systems are also disclosed.

5 Claims, 1 Drawing Sheet

OTHER PUBLICATIONS

Vaughn, J. L. et al., "The Establishment of Two Cell Lines from the Insect *Spodoptera frugiperda* (Lepidoptera; Noctuidae)", *In Vitro*, 13[4]:213–217 (1977).

Srinivasan, G. et al., "Overexpression of Full-length Human Glucocorticoid Receptor in *Spodoptera frugiperda* Cells Using the Baculovirus Expression Vector System", *Molec. Endocrin.* 4[2]:209–216 (1990).

Brown, M. et al., "Human Estrogen Receptor Forms Multiple Protein-DNA Complexes", *J. Biol. Chem.*, 265[19]:11238–11243 (1990).

Matsuura, Y. et al., "Baculovirus Expression Vectors: the Requirements for High Level Expression of Proteins, including Glycoproteins", *J. Gen. Virol.*, 68:1233–1250 (1987).

Summers, M. D., "Recombinant Proteins Expressed by Baculovirus Vectors", in *Concepts in Viral Pathogenesis III*, pp. 77–86 Springer-Verlag (1989).

Link, R. et al., "The Vitamin D Receptor", in *The Receptors, II*, pp. 1–35, Academic Press, (1985).

Brooks, M. H. et al., "Vitamin-D-Dependent Rickets Type II", *N. Engl. J. Med.*, 298[18]:996–999 (1978).

Eil, C. et al., "The Molecular Basis for Resistance to 1,25-dihydroxyvitamin D: Studies in Cells Cultured from Patients with Hereditary Hypocalcemic 1,25(OH)$_2$D$_3$-Resistant Rickets", *Adv. Exp. Med. Biol.*, 196:407–422 (1986).

Perlman, K. et al., "24-Homologated 1,25-Dihydroxyvitamin D$_3$ Compounds: Separation of Calcium and Cell Differentiation Activities", *Biochem.*, 29[1]:190–196 (1990).

Pike, J. W. et al., "Hormone-Dependent Phosphorylation of the 1,25-Dihydroxyvitamin D$_3$ Receptor in Mouse Fibroblasts", *Biochem. Biophys. Res. Commun.*, 131[1]:378–385 (1985).

Brown, T. A. et al., "Phosphorylation of the 1,25-Dihydroxyvitamin D$_3$ Receptor", *J. Biol. Chem.*, 265[17]:10025–10029 (1990).

Liao, J. et al., "Vitamin D Receptor Interaction with Specific DNA requires a Nuclear Protein and 1,25-Dihydroxyvitamin D$_3$", *Proc. Natl. Acad. Sci. USA*, 87:9751–9755 (1990).

Kerner, S. A. et al., "Sequence Elements in the Human Osteocalcin Gene Confer Basal Activation and Inducible Response to Hormonal Vitamin D$_3$", *Proc. Natl. Acad. Sci. USA, 86:4455–4459 (1989)*.

Demay, M. B. et al., "DNA Sequences in the Rat Osteocalcin Gene that Bind the 1,25-Dihydroxyvitamin D$_3$ Receptor and Confer Responsiveness to 1,25-Dihydroxyvitamin D$_3$", *Proc. Natl. Acad. Sci. USA*, 87:369–373 (1990).

Markose, E. R. et al., "Vitamin D-mediated Modifications In Protein-DNA Interactions at Two Promoter Elements of the Osteocalcin Gene", *Proc. Natl. Acad. Sci. USA*, 87:1701–1705 (1990).

Noda, M. et al., "Identification of a DNA Sequence Responsible for Binding of the 1,25-Dihydroxyvitamin D$_3$ enhancement of Mouse Secreted Phosphoprotein 1 (SPP-1 or Osteopontin) Gene Expression", *Proc. Natl. Acad. Sci. USA*, 87:9995–9999 (1990).

McDonnell, D. P. et al., "Reconstitution of the Vitamin D-Responsive Osteocalcin Transcription Unit in *Saccharomyces cerevisiae*", *Molecular and Cellular Biology*, 9[8]:3517–3523 (1989).

DeLuca, H. P., et al., "Vitamin D: Recent Advances", *Ann. Rev. Biochem.*, 52:411–439 (1983).

Norman, A. W., et al., "The Vitamin D Endocrine System: Steroid Metabolism, Hormone Receptors, and Biological Response (Calcium Binding Proteins)", *Endocr. Rev.*, 3[4]:331–366 (1982).

Omdahl, J. L. et al., "Regulation of Vitamin D Metabolism and Function", *Physiol. Rev.*, 53[2]:327–372 (1973).

Sutton, R. A. L., et al., "Effects of Vitamin D on Renal Tubular Calcium Transport", in *Vitamin D Biochemical, Chemical and Clinical Aspects Related to Calcium Metabolism*, Proceedings of the Third Workshop on Vitamin D, (1977).

Garabedian, M. et al., "Response of Intestinal Calcium Transport and Bone Calcium Mobilization to 1,25-Dihydroxyvitamin D$_3$ in Thyroparathyroidectomized Rats", *Endocrin.*, 94[4]:1022–1027 (1974).

OTHER PUBLICATIONS

Kleeman, C. R. et al., "Studies on the Renal Clearance of Diffusible Calcium and the Role of the Parathyroid Glands in its Regulation", in *The Parathyroids*, Proceedings of a Symposium on Advances in Parathyroid Research, Charles C. Thomas, Publ., (1961).

Hanahan, D., "Studies on Transformation of *Escherichia coli* with Plasmids", *J. Mol. Biol.*, 166:557-580 (1983).

Hanahan, D., "Techniques for Transformation of *E. coli*", *DNA Cloning I*, pp. 109-135, IRL Press (1985).

Vialard, J. et al., "Synthesis of the Membrane Fusion and Hemagglutinin Proteins of Measles Virus, Using a Novel Baculovirus Vector Containing the Beta-Galactosidase Gene", *J. Virol.*, 64[1]:37-50 (1990).

Laemmli, U. K., "Cleavage of Structural Proteins during the Assembly of the Head of Bacteriophage T4", *Nature*, 227:680-685 (1970).

Dame, M. C. et al., "Monoclonal Antibodies to the Porcine Intestinal Receptor for 1,25-Dihydroxyvitamin $D_3$ Interaction with Distinct Receptor Domains", *Biochem.*, 25:4523-4534 (1986).

Dame, M. C. et al., "Identification of the Porcine Intestinal 1,25-Dihydroxyvitamin $D_3$ Receptor on Sodium Dodecyl Sulfate/Polyacrylamide Gels by Renaturation and Immunoblotting", *Proc. Natl. Acad. Sci. USA*, 82:7825-7829 (1985).

Sandgren, M. E. et al., "An Immunoradiometric Assay for 1,25-Dihydroxyvitamin $D_3$ Receptor", *Anal. Biochem.*, 183:57-63 (1989).

Bradford, M. M., "A Rapid and Sensitive Method for the Quantitation of Microgram Quantities of Protein Utilizing the Principle of Protein-Dye Binding", *Anal. Biochem.*, 72:248-254 (1976).

Scatchard, G., "The Attractions of Proteins for Small Molecules and Ions", *Ann. N.Y. Acad. Sci.*, 51:660-672 (1949).

Napoli, J. L. et al., "Direct Chemical Synthesis of 1 alpha,25-Dihydroxy[26,27-$^3$H]vitamin $D_3$ with High Specific Activity: Its Use in Receptor Studies", *Biochem.*, 19:2515-2521 (1980).

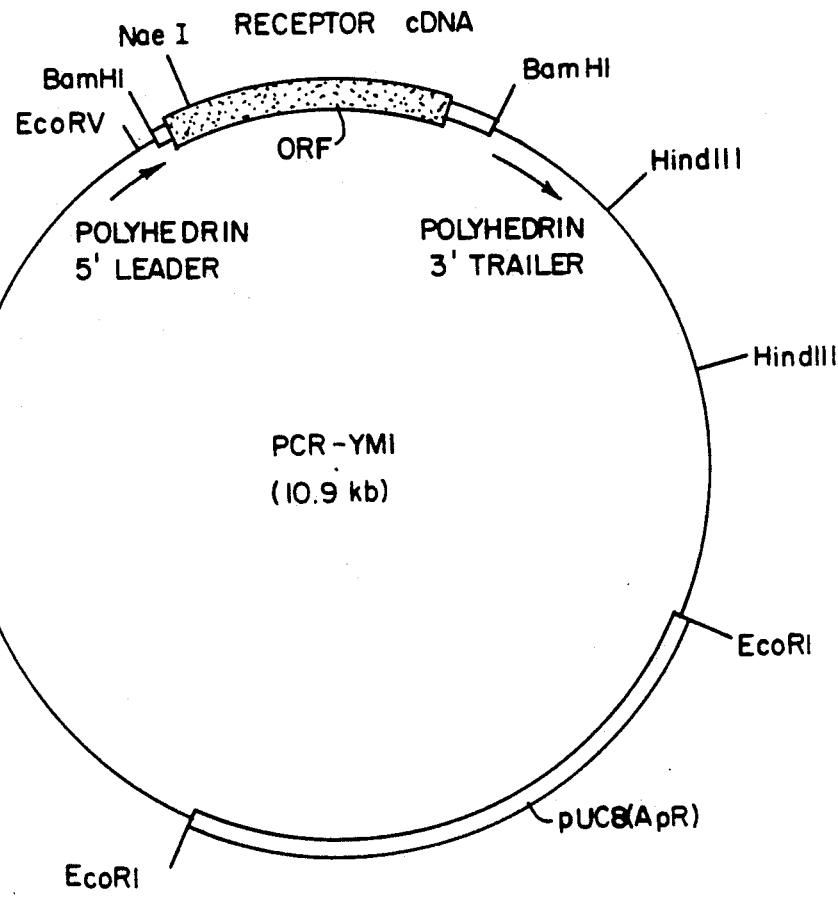

METHOD OF PRODUCING 1,25-DIHYDROXYVITAMIN D₃ RECEPTOR PROTEIN

FIELD OF THE INVENTION

The invention relates to improved techniques for producing and purifying vitamin $D_3$ receptor proteins through the use of recombinant DNA sequences.

BACKGROUND OF THE INVENTION 1,25-dihydroxyvitamin $D_3$ ("1,25-$(OH)_2D_3$"), the hormonal form of vitamin D, has several important biological activities in mammals. These activities include: (i) stimulation of intestinal calcium and phosphate transport from the lumen of the small intestine to the plasma; (ii) mobilization of calcium from bone to plasma; and (iii) reabsorption of calcium in the distal renal tubule. The biological activities of vitamin D ultimately lead to the elevation of plasma calcium and phosphorus levels which are necessary for bone mineralization and proper neuromuscular function.

The biological activities of 1,25-$(OH)_2D_3$ are mediated via intracellular receptor protein. DeLuca, H.F. et al., (1983) *Ann. Rev. Biochem.* 52, 411–439. (The disclosures of all articles recited herein are incorporated by reference as if fully set forth below.) The probable mechanism by which 1,25-$(OH)_2D_3$ elicits the intestinal calcium and phosphorus transport response consists of the 1,25-$(OH)_2D_3$ hormone entering the target cell and binding the nuclear receptor. The interaction of hormone with receptor may introduce changes in receptor conformation that allow the receptor to interact with chromatin. This interaction alters the expression of genes whose protein products influence functions such as calcium transport and mobilization. Link, R. et al. (1985) in *The Vitamin D Receptor*, Academic Press, New York, pp. 1–35.

Vitamin D-dependent rickets Type II is a disease that exemplifies the receptor-dependent function of 1,25-$(OH)_2D_3$. Bell, N.H. et al. (1978) *N. Engl. J. Med.* 298, 996–999. Patients with this disease suffer from hypocalcemia despite having elevated levels of 1,25-$(OH)_2D_3$ in their plasma because they have a target organ resistance to the hormonal derivative of vitamin D. A defect in the 1,25-$(OH)_2D_3$ receptor exists in at least one subgroup of rickets Type II patients. Eil, C., et al. (1986) *Adv. Exp. Med. Biol.* 196, 407–422.

The sequences for various animal vitamin D receptors are known. See McDonnell, D.P. et al., (1987) *Science* 235, 1214–1217 (Avian) (SEQ ID NO:3) Burmester, J.K., et al. (1988) *Proc. Natl. Acad. Sci. USA* 85, 1005–1009 (rat) (SEQ ID NO:4), and Baker, A.R. et al., (1988) *Proc. Natl. Acad. Sci. USA* 85, 3294–3298 (human)(SEQ ID NO:5). The amino acid sequences for these cDNAs have much in common. For example, the cDNAs display a cysteine-rich region at the amino terminus, characteristic of a DNA binding region. Also, the hydrophobic amino acids near the carboxy terminus form what is likely the hydrophobic pocket responsible for hormone binding. Domains within the human 1,25-$(OH)_2D_3$ receptor protein have been defined more precisely in McDonnell, D.P. et al., (1989) *Mol. Endocrinol.* 3, 635–644.

Discovery of cis-acting vitamin D-response elements (DRE) lying within the upstream regions of the human (Kerner, S.A., et al. (1989) *Proc. Natl. Acad. Sci. USA* 86, 4455–4459) and rat (Demay, M.B., et al. (1990) *Proc. Natl. Acad. Sci. USA* 87, 369–373, Markose, E.R. et al., (1990) *Proc. Natl. Acad. Sci. USA* 87, 1701–1705) osteocalcin genes, and the mouse osteopontin gene (Noda, M. et al., (1990) *Proc. Natl. Acad. Sci. USA* 87, 9995–9999) is consistent with 1,25-$(OH)_2D_3$ being a member of the steroid family of receptors. The sequences of other receptor DNA can now readily be determined using the existing sequences as hybridization probes against genomic and CDNA libraries, obtaining the cDNA using standard screening techniques, and then sequencing the DNA.

Lack of a low cost source of large amounts of 1,25-$(OH)_2D_3$ receptor has hindered commercial use and scientific studies of the receptor. For example, as disclosed in U.S. Pat. No. 4,816,417, 1,25-$(OH)_2D_3$ receptor is useful in an assay for 1,25-$(OH)_2D_3$.

Isolation of receptor from natural animal cells produces only very small quantities at very great cost. Dame, M. et al., (1986) *Biochemistry*, 25, 4523. The human 1,25-$(OH)_2D_3$ receptor has been expressed from full length DNA in *Saccharomyces cerevisiae* (yeast) cells. Sone, T., et al., (1990) *J. Biol. Chem.* 265, 21997–22003. However, the authors indicated potential problems in that the recombinant product upon purification lacked activities comparable to the natural receptor protein and amounts of receptor protein produced were quite low.

The need therefore exists for the creation of an improved method for expressing vitamin D receptor protein.

SUMMARY OF THE INVENTION

In one aspect, the present invention provides a method of producing 1,25-dihydroxyvitamin $D_3$ receptor protein. This method begins with the step of transcribing a DNA sequence to form an RNA sequence, the RNA sequence encoding animal vitamin D receptor. The receptor protein is then expressed from the RNA sequence. Less than the full natural 5' non-translated leader sequence is transcribed as part of the RNA sequence.

In a particularly advantageous embodiment, a 5' non-translated leader sequence on the RNA is less than 60% and more than 2% of the full natural 5' non-translated leader sequence. In another preferred embodiment, less than 90% of the full natural 3' non-translated flanking sequence is transcribed as part of the RNA.

In another aspect, the invention provides 1,25-dihydroxyvitamin $D_3$ receptor protein using the above methods.

In still another aspect, the invention provides an expression system for the production of 1,25-dihydroxyvitamin $D_3$ receptor protein. The system has an insect cell host and a recombinant virus. The virus contains a foreign DNA sequence encoding an RNA sequence which, when expressed in the insect cell host, produces 1,25-dihydroxyvitamin D receptor protein.

In yet another related aspect, the invention also provides a recombinant plasmid containing a DNA sequence encoding 1,25-dihydroxyvitamin $D_3$ receptor protein, the DNA sequence containing a 5' non-translated sequence that when transcribed to RNA produces an RNA sequence that has less than the full 5' leader sequence present in the natural form of the RNA sequence.

An object of the present invention is to produce 1,25-(OH)₂D₃ receptor protein at low cost and in high quantity.

Another object is to produce the receptor protein in a biologically active state.

Another object of the invention is to express receptor protein that is at least 5% of the total soluble protein extracted from host expressing cells.

BRIEF DESCRIPTION OF THE DRAWINGS

FIG. 1 depicts rat 1,25-(OH)₂D₃ receptor CDNA. The arrows labeled I and II denote the location of the sequences from which the synthetic oligonucleotide primers were derived. The position of a unique Nae I restriction site is also indicated;

FIG. 2 describes the nucleotide sequence of primers that were used in the PCR amplification of the 1,25-(OH)₂D₃ receptor open reading frame (ORF). Artificial BamH I recognition sequences are highlighted. Random tailing sequences are shown in lower case letters; and FIG. 3 is a schematic representation of recombinant plasmid PCR-YM1, which consists of the segment of receptor CDNA inserted to plasmid vector pAcYM1.

DESCRIPTION OF THE PREFERRED EMBODIMENTS

The description of the preferred embodiments below are examples of the invention. They are not, however, intended to represent the full scope of the invention. The claims should be examined to determine the full scope of the invention.

1. Overview

As an example, we chose to express modified rat receptor DNA in a baculovirus expression system. Receptor DNA sequences from other animals that have been modified in accordance with the present invention are equally suitable for the practice of the present invention.

Baculovirus vector/insect cell expression systems have been used to express certain other CDNAS. See Luckow, V.A., (1990) in *Recombinant DNA Technology And Applications*, McGraw-Hill, N.Y. pp. 1-25; Summers, M. & Smith, G.E. (1987) *A Manual of Methods for Baculovirus Vectors and Insect Cell Culture Procedures*, Texas Agricultural Experiment Station and Texas A & X University, College Station, Tex.; and Summers, M.D. (1989) in *Concepts in Viral Pathogenesis*, N.Y. pp. 77-86. However, there are no previous reports of such systems being successfully used to express vitamin D₃ receptor protein, and our attempts to express natural vitamin D₃ receptor DNA in such baculovirus systems were not successful.

We then created a plasmid containing modified receptor cDNA. A problem we faced in making modifications was that the sequence of the CDNA indicated that there were no convenient restriction sites where we wanted to modify. We therefore used a special adaptation of polymerase chain reaction to construct a version of the receptor CDNA with truncated 5' and 3' untranslated flanking sequences and cloned this truncated CDNA segment into a plasmid vector. We then cotransfected this plasmid with DNA from ACNDV, a wild-type baculovirus, into Sf21 insect cells. Co-transfection produced a recombinant baculovirus containing the receptor segment. The recombinant virus was identified by a unique visual screening technique for plaque morphology and purified through three rounds of plaque purification.

2. Construction Of Recombinant Plasmid Transfer Vector PCR-YM1

Plasmid pRDR26 is a pUC18 derivative harboring a 2043 base pair (bp) rat 1,25-(OH)₂D₃ receptor CDNA. The 2043 bp segment is illustrated in FIG. 1. This CDNA is believed to contain complete 5' and 3' untranslated regions and the receptor protein-encoding region. The construction of this plasmid, together with the nucleotide sequence of the rat CDNA (SEQID NO:6), has been described Bummester, J.K. et al., (1988) *Proc. Natl. Acad. Sci. USA* 85, 9499-9502.

Our belief is that the non-translated sequences of the receptor DNA needs some length for message stability, but that too much length destroys expression. The rat receptor 5' nontranslated leader sequence is 94 bp (FIG. 1.). We decided to shorten it to 45 bp and to add a BAMH I site to permit cloning. We also decided to shorten the 3' nontranslated sequence to 300 bp.

Unfortunately, as indicated above, these non-translated regions lacked convenient restriction enzyme recognition sites. We chose to create a "truncated" modified CDNA by amplifying only a defined segment of the known CDNA using a modification of polymerase chain reaction techniques. This approach circumvented the restriction site problem.

For this purpose oligonucleotide primers were synthesized as follows: Primer I contained nucleotides -45 to -23, and Primer II contained nucleotides 1569 to 1547. FIG. 2 describes these primers. Primer I is SEQ ID WO:1 and Primer II is SEQ ID NO:2 in the Sequence Listing below. Both primers were synthesized with both the recognition sequence for BamH I and 8 nucleotides of random sequence at their 5' termini.

To perform the PCR-mediated truncation, we first transformed *E. coli* strain DH5α (Manahan, D. (1983) *J. Mol. Biol.* 166, 557-580) with pRDR26, and a single colony was transferred into 150 μl H₂O to make a homogeneous cell suspension. Fifteen μl of the cell suspension were added to the following PCR reaction components: 1 μM primer I, 1 μM primer II, 1x Taq polymerase reaction buffer, 2 units Taq polymerase (Promega Corp., Madison, Wis.), and 200 nM deoxynucleotide triphosphates (DATP, DGTP, DCTP, and dTTP) in a total reaction volume of 100 pl. A Perkin Elmer Cetus, DNA Thermal Cycler was used to change the reaction temperature. We used the following time and temperature parameters: 94° C. for 1 min., 20 cycles [94° C. for 1 min., 55° C. for 1 min., 72° C. for 1.5 min.], 72° C. for 5 min., storage at 4° C.

An aliquot of the amplified DNA was treated with BamH I to generate the appropriate cohesive restriction termini and then ligated with 1 μg of BamH I-digested plasmid transfer vector pAcYM1 (Matsuura, Y. et al., (1987), *J. Gen. Virol.* 68, 1233-1250) in the presence of T4 DNA ligase for 18 hours at 16° C. Vector pAcYM1 contains polyhedron sequences that permit recombination with a wild-type baculovirus. Vector pAcYM1 is available from Dr. D.H.L. Bishop (NERC Institute of Virology, Oxford, U.K.).

A portion of the ligated mixture was used to transform competent cells of strain DH5α to ampicillin resistance (Ap^R) (Hanahan, D. (1985) in *DNA Cloning: A Practical Approach*, IRL Press, Oxford, p. 109). Small-scale isolation and restriction analysis of plasmid DNAs from several Ap^R transformants revealed four having the proper PCR-amplified product contained within the pAcYN1 vector. We identified a recombinant plasmid with the insert DNA in the proper orientation with respect to the polyhedrin gene signals from pAcYM1 by using several different combinations of restriction endonuclease digestions, and subsequent analysis by agarose gel electrophoresis. The recombinant plasmid transfer vector was designated PCR-Ym1. FIG. 3 illustrates PCR-YM1. For other CDNA (e.g. avian, human, pig) trancation/modifications can be achieved in similar fashion.

3. Generation Of Recombinant Baculovirus DR-AcNPV

AcNPV is a wild-type baculovirus. It is commercially available from InVitroGen Corp. (San Diego, Calif.). Upon co-transfection of an insect host with a plasmid containing a foreign gene flanked by polyhedron sequences, a recombinant baculovirus will be formed. The co-transfections and protein expression can be done in various insect cells, such as Sf21 cells. Sf21 cells are insect cells commonly used for the baculovirus expression system and are also commercially available from InVitroGen Corp. (San Diego, Calif.).

We performed the co-transfection as follows: Fifteen μg PCR-YM1 plasmid DNA, purified by ethidium bromide-CsCl equilibrium density gradient centrifugation, was added to 1 μg wild-type ACNPV DNA (Granados, R.R.-et al., (1986) in *Biological Properties and Molecular Biology*, CRC, Boca Raton, Fla., vol. 1, pp. 90–127) and transfected into SF21 cells (Vaugh, J.L. et al., (1977) In Vitro 13, 213-217) using the Lipofectin (Gibco BRL/Life Technologies, Inc, Gaithersburg, Md.) reagent according to the manufacturer's specifications. The Sf21 (*Spodoptera frugiperda*) insect cells and wild-type ACNPV (*Autographs californica* nuclear polyhedrosis virus) that we used were gifts from Dr. Paul Friesen (Dept. of Biochemistry, University of Wisconsin, Madison, Wis.).

After a 96-hour incubation of the co-transfection mixture at 27° C., the viral supernatant was harvested as in Summers et al. (above). This supernatant contained both recombinant and non-recombinant virion particles. Dilutions of this viral preparation were used to infect freshly plated Sf21 cells according to the agarose overlay procedure (Summers et al., above). Plaques derived from a potential occlusion deficient, recombinant virus were picked and purified through three rounds of purification. We confirmed that we had created recombinant virus DR-AcNpv, containing the 1,25-$(OH)_2D_3$ receptor coding region, by hybridization screening (Summers et al., above).

We have deposited DR-ACNPV with American Type Culture Collection 12301 Parklawn Drive, Rockville, Md., U.S.A., as ATCC No. VR2334, on Jul. 26, 1991. Samples from the deposit are available in accordance with U.S. patent law requirements upon issuance of the patent and the requirements of any applicable foreign patent laws. No patent license is intended by such availability.

4. Preparation Of Protein Extracts From Infected Insect Cells

Sf21 cells were plated at a density of $3 \times 10^6$ per 100 nm plate in TC100 (Gibco BRL) insect cell media and allowed to attach for 30 to 60 min. The medium was removed and 1 ml of either DR-ACNPV or ACNPV (multiplicity of infection=1 to 10) was added to the surface of the cell monolayer. (AcNPV, the wild-type virus, was added as a control.) The cells were maintained at 27° C. with gentle rocking for 60 min. This was followed by the addition of 5 ml of TC100 media supplemented with 10% fetal calf serum and continued incubation at 27° C. Cells were harvested 72 hr after infection with virus unless otherwise noted.

Extracts of soluble protein were prepared by first disrupting the infected cells by repeated pipetting and washing of the plate surface. The suspended cells were transferred to a plastic conical tube and collected by centrifugation at 500 x g for 10 min. The medium was discarded and the cells were suspended in TEDK$_{20}$ [50 mM Tris-HCl, pH 7.4/1.5 mM EDTA/5 mM dithiothreitol/20 mM KCl] containing 1 mM phenylmethylsulfonyl fluoride (PMSF), 5 mM diisopropylfluorophosphate (DFP), and 1 μg/ml pepstatin. The cell suspension was incubated for 30 min on ice before homogenization in a stainless steel Dounce homogenizer (3 strokes). Enough TED buffer, containing 600 mM KCl, was added to bring the final KCl concentration to 300 mM. The cells were homogenized with 3 additional strokes and the homogenate was centrifuged for 60 min at 45,000 rpm in a Beckman 70.1 Ti rotor. The cleared supernatant was divided into small aliquots and quick-frozen in liquid nitrogen. Storage of the extracts was at −70° C.

5. Gel Electrophoresis Analysis Of Protein Extracts

We analyzed both total cell protein and soluble cell protein via gel electrophoresis. The soluble cell protein is that obtained by the method described above. Total cellular protein extracts were prepared by infecting and harvesting the cells as described above. The cells, collected by centrifugation, were lysed in 4% SDS, electrophoresis sample buffer. Vialard, J. et al., (1990) *J. Virol.* 64, 37-50. Total protein extracts or total soluble protein extracts were mixed with electrophoresis buffer (Laemmli U.K. (1970) *Nature* 227, 680-685) and boiled for 1 min. The protein samples were electrophoresed on 9% SDS-polyacrylamide gels.

Confirmation of rat 1,25-$(OH)_2D_3$ receptor protein production in infected insect cells was obtained by SDS-polyacrylamide gel analysis of cell extracts. We observed that a prominant band at Mr 55,000 evident in the extract from cells infected with DA-ACNPV is not present in the extract from Sf21 cells or the extract from Sf21 cells infected with wild-type AcNPV. We believe that this Mr 55,000 band is due to the receptor protein.

6. Measurement Of 1,25-$(OH)_2D_3$ Receptor Via Hydroxylapatite Binding And Immunoradiometric Assay The 1,25-$(OH)_2$-$(26,27-^3H]D_3$ binding activity in total soluble protein extracts from DR-AcNPV-infected Sf21 cells was determined by a hydroxylapatite binding assay as previously described in Dame et al., (1985) *Proc. Natl. Acad. Sci. USA* 82, 7823-7829. Total 1,25-$(OH)_2D_3$ receptor was determined by an immunoradiometric assay (IRMA). Sandgren, M. et al., (1989) *Anal. Biochem.* 183, 57-63. Protein content of the extracts was measured by the Bradford method. Bradford, M.M. (1976) *Anal. Biochem.* 72, 248-254. 1,25-$(OH)_2D_3$ was a gift from the Hoffmann-LaRoche Co. (Nutley, N.J.). 1,25-$(OH)_2$-$[26,27-^3H]D_3$ (160 Ci/mmol; 1 Ci=37 GBq) was produced by Dupont/NEN (Boston, Mass.) as described. Napoli, J.L. et al., (1980) *Biochemistry* 19, 2515-2521.

Table 1 (following) describes the results of quantification of recombinant 1,25-$(OH)_2D_3$ receptor using the hydroxylapatite ligand-binding assay and the ligand-independent, immunoradiometric assay. The level of receptor per weight of material was determined to be nearly 1500 times greater when derived from our method than from the prior art pig nuclear extract (1.35 pmol/mg).

TABLE 1

Measurements of 1,25-(OH)$_2$D$_3$ Receptor[a]

| Sample | Ligand Binding Assay[b] (pmol/mg protein) | IRMA[c] (pmol/mg protein) |
|---|---|---|
| Recombinant DR-AcNPV/Sf21 Cytosol | 2,000 ± 1,000 | 2,300 ± 1,000 |
| Pig Intestinal Nuclear Extract | 1.35 ± 0.15 | 1.68 ± 0.12 |

[a]These levels represent an average of measurements performed in triplicate on six different cytosolic preparations.
[b]Obtained using the hydroxylapatite assay.
[c]Obtained using the immunoradiometric assay.

7. Characteristics Of The Recombinant 1,25-(OH)$_2$D$_3$ Receptor a. Scatchard Analysis We confirmed that our receptor protein binds to vitamin D with a binding constant similar to that of natural receptor. A 1,25-(OH)$_2$D$_3$ saturation analysis of cytosol from DR-AcNPV-infected Sf$_2$l cells was plotted by the method of Scatchard. The equilibrium dissociation constant (Kd), calculated by linear regression, was $1 \times 10^{-11}$M. The Kd value is consistent with the reported measurements of $10^{-10}$ to $10^{-11}$M for the hormone-receptor complex in crude preparations. Link, R. et al. (1985) in *The Vitamin D Receptor*, Academic Press, New York, pp. 1–35.

b. Western Blot Analysis

We then confirmed that our receptor bound to antibody to natural rat receptor, but not to antibody specific for pig receptor. Samples containing both recombinant and non-recombinant 1,25-(OH)$_2$D$_3$ receptor were electrophoresed on polyacrylamide gels. The proteins were immobilized on filters and the filters were blocked with Tris-buffered saline/Tween 20 (TBST) containing 5% nonfat dry milk. The filters were then incubated with primary antibody for 90 min. The filters were washed extensively in TBST and then incubated with a secondary alkaline-phosphatase-conjugated goat anti-mouse IgG antibody. The color was developed with nitrobluetetrazolium/5-bromo-4-chloro-3-indolylphosphate substrate using the ProtoBlot AP system according to manufacturer's specifications (Promega Corp., Madison, Wis.). Monoclonal anti-receptor antibody preparation has been described in Dame, et al., (1986) *Biochemistry* 25, 4523–4534).

Monoclonal antibody IVG8C11, known to cross-react with 1,25-(OH)$_2$D$_3$ receptor from pig, rat, monkey, human and chicken (Dame, M.C. et al., (1986) *Biochemistry* 25, 4523–4534), was used in the Western analysis of extract from Sf21 cells. IVG8C11 reacted with our recombinant receptor.

An identical blot was analyzed with the monoclonal antibody XVIE10B6A5 as the primary antibody. This anti-receptor antibody is known to react only with porcine-derived 1,25-(OH)$_2$D$_3$ receptor. Dame, M.C. et al., (1986) *Biochemistry* 25, 4523–4534. The Western analysis using XVIE10B6A5 showed no reactivity with the extract from DR-AcNPV-infected Sf21 cells.

In summary, the present invention solves the problems in prior art methods of producing 1,25-(OH)$_2$D$_3$ receptor. In our experiments, the present invention produced 2,000 pmol/mg cellular protein of receptor that reacts with activity like the natural protein. This quantity and quality of protein should be compared to the reported 100 pmol/mg cellular protein produced in the yeast system, which upon purification did not have activities comparable to wild type activities, and the 1.35 pmol/mg cellular protein our lab reported producing from the natural pig intestinal nuclear extract system.

8. Other Systems

While rat, human, avian, and porcine receptors are preferred, the method of the present invention should be applicable for expression of receptor protein derived from other animal (e.g. mammalian and avian) systems. A CDNA encoding the receptor will typically first be isolated from the animal cells using known receptor fragments as probes. Once a CDNA sequence is obtained, it will then be sequenced using standard techniques and the sequence must be modified according to the method of the present invention. The 3' and 5' non-translated flanking sequences should preferably be truncated by between 90% and 2%. More preferably, the 5' untranslated sequence is shortened to approximately 45 nucleotides and the 3' untranslated sequence is shortened to approximately 300 nucleotides. A plasmid containing this truncated CDNA will then be co-transfected with baculovirus. Co-transfection will produce a recombinant virus. This virus can be used to infect insect cells, and the recombinant protein can be expressed.

We claim:

1. A method of producing 1,25-dihydroxyvitamin D3 receptor protein, comprising the steps of:
   transcribing a DNA sequence from a recombinant vector to form an RNA, the RNA encoding animal vitamin D receptor; and
   then expressing the receptor protein from the RNA;
   wherein the RNA transcribed from the DNA sequence has a 5' non-translated 1,25-dihydroxyvitamin D3 receptor leader sequence of between 38 and 56 nucleotides; and wherein the DNA sequence is positioned in a recombinant virus and the expression step takes place in an insect host cell.

2. The method of claim 1, wherein the RNA has a 5' non-translated leader sequence that is equal to about 45 nucleotides and wherein the expression step takes place in a baculovirus expression system.

3. The method of claim 1 wherein the RNA transcribed from the DNA sequence has 3' non-translated 1,25-dihydroxyvitamin D3 receptor sequence of about 300 nucleotides.

4. An expression system for the production of 1,25-dihydroxyvitamin D3 receptor protein, comprising:
   an insect cell host; and
   a recombinant virus;
   said virus containing a foreign DNA sequence encoding an RNA which, when expressed in the insect cell host, produces 1,25-dihydroxyvitamin D3 receptor protein, wherein the expressed RNA has a 5' non-translated 1,25-dihydroxyvitamin D3 receptor leader sequence of between 56 and 38 nucleotides.

5. The system of claim 4 wherein the recombinant virus is a baculovirus containing a foreign DNA sequence.

* * * * *

UNITED STATES PATENT AND TRADEMARK OFFICE
CERTIFICATE OF CORRECTION

PATENT NO. : 5,260,199
DATED : November 9, 1993
INVENTOR(S) : Hector F. DeLuca, et al.

Page 1 of 2

It is certified that error appears in the above-indentified patent and that said Letters Patent is hereby corrected as shown below:

| | |
|---|---|
| Column 2, line 9 | "CDNA" s/b "cDNA" |
| Column 2, line 18 | "Isolation-of" s/b "Isolation of" |
| Column 3, line 11 | "CDNA" s/b "cDNA" |
| Column 3, line 24 | "CDNA" s/b "cDNA" |
| Column 3, line 42 | "CDNAs" s/b "cDNAs" |
| Column 3, line 48 | "A & X" s/b "A & M" |
| Column 3, line 58 | "CDNA" s/b "cDNA" |
| Column 3, line 61 | "CDNA" s/b "cDNA" |
| Column 3, line 63 | "CDNA" s/b "cDNA" |
| Column 3, line 64 | "ACDNV" s/b "AcDNV" |
| Column 4, line 6 | "CDNA" s/b "cDNA" |
| Column 4, line 8 | "CDNA" s/b "cDNA" |
| Column 4, line 11 | "CDNA" s/b "cDNA" |
| Column 4, line 24 | "CDNA" s/b "cDNA" |
| Column 4, line 25 | "CDNA" s/b "cDNA" |
| Column 4, line 32 | "WO:1" s/b "NO:1" |
| Column 4, line 45 | "DATP, DGTP, DCTP" s/b "dATP, dGTP, dCTP" |
| Column 4, line 46 | "100 pl" s/b "100 µl" |
| Column 5, line 7 | "PCR-Yml" s/b "PCR-YM1" |
| Column 5, line 8 | "CDNA" s/b "cDNA" |
| Column 5, line 27 | "ACNPV" s/b "AcNPV" |
| Column 5, line 35 | "ACNPV" s/b "AcNPV" |
| Column 5, line 35 | "Autographs" s/b "Autographa" |
| Column 5, line 49 | "DR-AcNpv" s/b "DR-AcNPV" |
| Column 5, line 52 | "DR-ACNPV" s/b "DR-AcNPV" |
| Column 5, line 63 | "nm" s/b "mm" |
| Column 5, line 65 | "DR-ACNPV" s/b "DR-AcNPV" |
| Column 5, line 65 | "ACNPV" s/b "AcNPV" |
| Column 6, line 43 | "DA-ACNPV" s/b "DR-AcNPV" |
| Column 7, line 23 | "Sf$_2$1" s/b "Sf21" |
| Column 8, line 33 | "CDNA" s/b "cDNA" |
| Column 8, line 35 | "CDNA" s/b "cDNA" |

UNITED STATES PATENT AND TRADEMARK OFFICE
CERTIFICATE OF CORRECTION

PATENT NO. : 5,260,199
DATED : November 9, 1993
INVENTOR(S) : Hector F. DeLuca, et al.

It is certified that error appears in the above-indentified patent and that said Letters Patent is hereby corrected as shown below:

Column 8, line 40     "$_2$%" s/b "2%"
Column 8, line 44     "CDNA" s/b "cDNA"

In the sequences:
COL. 9, SEQ ID NO:3     "OBert W." s/b "O'Malley, Bert W."

COL. 13, SEQ ID NO:5     "OBert W." s/b "O'Malley, Bert W."

Signed and Sealed this

Twenty-seventh Day of December, 1994

Attest:

BRUCE LEHMAN

Attesting Officer      Commissioner of Patents and Trademarks

UNITED STATES PATENT AND TRADEMARK OFFICE
CERTIFICATE OF CORRECTION

| | | |
|---|---|---|
| PATENT NO. | : | 5,260,199 |
| DATED | : | November 9, 1993 |
| INVENTOR(S) | : | Hector F. DeLuca, et al. |

It is certified that error appears in the above-identified patent and that said Letters Patent is hereby corrected as shown below:

At Column 1, line 5, please insert the following:

This invention was made with United States Government support awarded by the National Institutes of Health (NIH), Grant Nos. DK-14881 and DK-08424. The United States Government has certain rights in this invention.

Signed and Sealed this

Thirteenth Day of June, 1995

Attest:

BRUCE LEHMAN

*Attesting Officer* — *Commissioner of Patents and Trademarks*

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( i i i ) HYPOTHETICAL: YES ( i v ) ANTI-SENSE: NO ( x ) PUBLICATION INFORMATION:
( A ) AUTHORS: Ross, Troy K.

-continued

Prahl, Jean M.
     DeLuca, Hector F.
   ( B ) TITLE: Overproduction of rat 1,25-dihydroxyvitamin
     D3 receptor in insect cells using the baculovirus
     expression system
   ( C ) JOURNAL: Proc. Natl. Acad. Sci. U.S.A.
   ( D ) VOLUME: 88
   ( F ) PAGES: 6555-6559
   ( G ) DATE: August-1991
   ( K ) RELEVANT RESIDUES IN SEQ ID NO:1: FROM 1 TO 37

( x i ) SEQUENCE DESCRIPTION: SEQ ID NO:1:

CGAGCCGGGG ATCCTCCAGG AGAGCACCCT TGGGCTC                   37

( 2 ) INFORMATION FOR SEQ ID NO:2:

( i ) SEQUENCE CHARACTERISTICS:
   ( A ) LENGTH: 37 base pairs
   ( B ) TYPE: nucleic acid
   ( C ) STRANDEDNESS: single
   ( D ) TOPOLOGY: linear ( i i i ) HYPOTHETICAL: YES ( i v ) ANTI-SENSE: NO ( x ) PUBLICATION INFORMATION:
   ( A ) AUTHORS: Ross, Troy K
     Prahl, Jean M
     DeLuca, Hector F
   ( B ) TITLE: Overproduction of rat 1,25-dihydroxyvitamin
     D3 receptor in insect cells using the baculovirus
     expression system
   ( C ) JOURNAL: Proc. Natl. Acad. Sci. U.S.A.
   ( D ) VOLUME: 88
   ( F ) PAGES: 6555-6559
   ( G ) DATE: August-1991
   ( K ) RELEVANT RESIDUES IN SEQ ID NO:2: FROM 1 TO 37

( x i ) SEQUENCE DESCRIPTION: SEQ ID NO:2:

CGAGCCGGGG ATCCAGTTCC GCCTTCAGCC CCTGCCC                   37

( 2 ) INFORMATION FOR SEQ ID NO:3:

( i ) SEQUENCE CHARACTERISTICS:
   ( A ) LENGTH: 70 amino acids
   ( B ) TYPE: amino acid
   ( C ) STRANDEDNESS: single
   ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
   ( A ) ORGANISM: Chicken ( x ) PUBLICATION INFORMATION:
   ( A ) AUTHORS: McDonnell, Donald P.
     Mangelsdorf, David J.
     Pike, J. W.
     Haussler, Mark R.
     OBert W.
   ( B ) TITLE: Molecular Cloning of Complementary DNA
     Encoding the Avian Receptor for Vitamin D
   ( C ) JOURNAL: Science
   ( D ) VOLUME: 235
   ( F ) PAGES: 1214-1217
   ( G ) DATE: March 6-1987

( x i ) SEQUENCE DESCRIPTION: SEQ ID NO:3:

Arg Ile Cys Gly Val Cys Gly Asp Arg Ala Thr Gly Phe His Phe Asn
1     5          10          15

Ala Met Thr Cys Glu Gly Cys Lys Gly Phe Phe Arg Arg Ser Met Lys

|  | 20 |  |  |  | 25 |  |  |  |  | 30 |  |  |
|---|---|---|---|---|---|---|---|---|---|---|---|---|

```
Arg Lys Ala Met Phe Thr Cys Pro Phe Asn Gly Asp Cys Lys Ile Thr
        35                  40                  45

Lys Asp Asn Arg Arg His Cys Gln Ala Cys Arg Leu Lys Arg Cys Val
    50                  55                  60

Asp Ile Gly Met Met Lys
65              70
```

(2) INFORMATION FOR SEQ ID NO:4:

(i) SEQUENCE CHARACTERISTICS:
        (A) LENGTH: 367 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: Rat (x) PUBLICATION INFORMATION:
        (A) AUTHORS: Burmester, James K.
                  Maeda, Nobuyo
                  DeLuca, Hector F.
        (B) TITLE: Isolation and expression of rat
               1,25- dihydroxyvitamin D3 receptor cDNA
        (C) JOURNAL: Proc. Natl. Acad. Sci. U.S.A.
        (D) VOLUME: 85
        (F) PAGES: 1005-1009
        (G) DATE: February-1988

(xi) SEQUENCE DESCRIPTION: SEQ ID NO:4:

```
Arg Phe Thr Cys Pro Phe Asn Gly Asp Cys Arg Ile Thr Lys Asp Asn
1               5                   10                  15

Arg Arg His Cys Gln Ala Cys Arg Leu Lys Arg Cys Val Asp Ile Gly
            20                  25                  30

Met Met Lys Glu Phe Ile Leu Thr Asp Glu Glu Val Gln Arg Lys Arg
        35                  40                  45

Glu Met Ile Met Lys Arg Lys Glu Glu Glu Ala Leu Lys Asp Ser Leu
    50                  55                  60

Arg Pro Lys Leu Ser Glu Glu Gln Gln His Ile Ile Ala Ile Leu Leu
65                  70                  75                  80

Asp Ala His His Lys Thr Tyr Asp Pro Thr Tyr Ala Asp Phe Arg Asp
                85                  90                  95

Phe Arg Pro Pro Val Arg Met Asp Gly Ser Thr Gly Ser Tyr Ser Pro
            100                 105                 110

Arg Pro Thr Leu Ser Phe Ser Gly Asn Ser Ser Ser Ser Ser Ser Asp
        115                 120                 125

Leu Tyr Thr Thr Ser Leu Asp Met Met Glu Pro Ser Gly Phe Ser Asn
    130                 135                 140

Leu Asp Leu Asn Gly Glu Asp Ser Asp Asp Pro Ser Val Thr Leu Asp
145                 150                 155                 160

Leu Ser Pro Leu Ser Met Leu Pro His Leu Ala Asp Leu Val Ser Tyr
                165                 170                 175

Ser Ile Gly Lys Val Ile Gly Phe Ala Lys Met Ile Pro Gly Phe Arg
            180                 185                 190

Asp Leu Thr Ser Asp Asp Gln Ile Val Leu Leu Lys Ser Ser Ala Ile
        195                 200                 205

Glu Val Ile Met Leu Arg Ser Asn Gln Ser Phe Thr Met Asp Asp Met
```

|  |  |  |  |  | 210 |  |  |  |  | 215 |  |  |  |  | 220 |  |  |
|---|---|---|---|---|---|---|---|---|---|---|---|---|---|---|---|---|---|
| Ser | Trp | Asp | Cys | Gly | Ser | Gln | Asp | Tyr | Lys | Tyr | Asp | Val | Thr | Asp | Val |  |  |
| 225 |  |  |  |  | 230 |  |  |  |  | 235 |  |  |  |  | 240 |  |  |
| Ser | Lys | Ala | Gly | His | Thr | Leu | Glu | Leu | Ile | Glu | Pro | Leu | Ile | Lys | Phe |  |  |
|  |  |  |  | 245 |  |  |  |  | 250 |  |  |  |  | 255 |  |  |  |
| Gln | Val | Gly | Leu | Lys | Lys | Leu | Asn | Leu | His | Glu | Glu | Glu | His | Val | Leu |  |  |
|  |  |  |  | 260 |  |  |  |  | 265 |  |  |  |  | 270 |  |  |  |
| Leu | Met | Ala | Ile | Cys | Ile | Val | Ser | Pro | Asp | Arg | Pro | Gly | Val | Gln | Asp |  |  |
|  |  |  | 275 |  |  |  |  | 280 |  |  |  |  | 285 |  |  |  |  |
| Ala | Lys | Leu | Val | Glu | Ala | Ile | Gln | Asp | Arg | Leu | Ser | Asn | Thr | Leu | Gln |  |  |
|  |  | 290 |  |  |  |  | 295 |  |  |  |  | 300 |  |  |  |  |  |
| Thr | Tyr | Ile | Arg | Cys | Arg | His | Pro | Pro | Pro | Gly | Ser | His | Gln | Leu | Tyr |  |  |
| 305 |  |  |  |  | 310 |  |  |  |  | 315 |  |  |  |  | 320 |  |  |
| Ala | Lys | Met | Ile | Gln | Lys | Leu | Ala | Asp | Leu | Arg | Ser | Leu | Asn | Glu | Glu |  |  |
|  |  |  |  | 325 |  |  |  |  | 330 |  |  |  |  | 335 |  |  |  |
| His | Ser | Lys | Gln | Tyr | Arg | Ser | Leu | Ser | Phe | Gln | Pro | Glu | Asn | Ser | Met |  |  |
|  |  |  | 340 |  |  |  |  | 345 |  |  |  |  | 350 |  |  |  |  |
| Lys | Leu | Thr | Pro | Leu | Val | Leu | Glu | Val | Phe | Gly | Asn | Glu | Ile | Ser |  |  |  |
|  |  |  | 355 |  |  |  |  | 360 |  |  |  |  | 365 |  |  |  |  |

( 2 ) INFORMATION FOR SEQ ID NO:5:

( i ) SEQUENCE CHARACTERISTICS:
        ( A ) LENGTH: 1399 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens ( x ) PUBLICATION INFORMATION:
        ( A ) AUTHORS: Baker, Andrew R.
            McDonnell, Donald P.
            Hughes, Mark
            Crisp, Tracey M.
            Mangelsdorf, David J.
            Haussler, Mark R.
            Pike, J. W.
            Shine, John
            OBert W.
        ( B ) TITLE: Cloning and expression of full-length cDNA
            encoding human vitamin D receptor
        ( C ) JOURNAL: Proc. Natl. Acad. Sci. U.S.A.
        ( D ) VOLUME: 85
        ( F ) PAGES: 3294-3298
        ( G ) DATE: May-1988

( x i ) SEQUENCE DESCRIPTION: SEQ ID NO:5:

```
GGAACAGCTT  GTCCACCCGC  CGGCCGGACC  AGAAGCCTTT  GGGTCTGAAG  TGTCTGTGAG        60

ACCTCACAGA  AGAGCACCCC  TGGGCTCCAC  TTACCTGCCC  CCTGCTCCTT  CAGGGATGGA       120

GGCAATGGCG  GCCAGCACTT  CCCTGCCTGA  CCCTGGAGAC  TTTGACCGGA  ACGTGCCCCG       180

GATCTGTGGG  GTGTGTGGAG  ACCGAGCCAC  TGGCTTTCAC  TTCAATGCTA  TGACCTGTGA       240

AGGCTGCAAA  GGCTTCTTCA  GGCGAAGCAT  GAAGCGGAAG  GCACTATTCA  CCTGCCCCTT       300

CAACGGGGAC  TGCCGCATCA  CCAAGGACAA  CCGACGCCAC  TGCCAGGCCT  GCCGGCTCAA       360

ACGCTGTGTG  GACATCGGCA  TGATGAAGGA  GTTCATTCTG  ACAGATGAGG  AAGTGCAGAG       420

GAAGCGGGAG  ATGATCCTGA  AGCGGAAGGA  GGAGGAGGCC  TTGAAGGACA  GTCTGCGGCC       480
```

| | | | | | | |
|---|---|---|---|---|---|---|
| CAAGCTGTCT | GAGGAGCAGC | AGCGCATCAT | TGCCATACTG | CTGGACGCCC | ACCATAAGAC | 540 |
| CTACGACCCC | ACCTACTCCG | ACTTCTGCCA | GTTCCGGCCT | CCAGTTCGTG | TGAATGATGG | 600 |
| TGGAGGGAGC | CATCCTTCCA | GGCCCAACTC | CAGACACACT | CCCAGCTTCT | CTGGGGACTC | 660 |
| CTCCTCCTCC | TGCTCAGATC | ACTGTATCAC | CTCTTCAGAC | ATGATGGACT | CGTCCAGCTT | 720 |
| CTCCAATCTG | GATCTGAGTG | AAGAAGATTC | AGATGACCCT | TCTGTGACCC | TAGAGCTGTC | 780 |
| CCAGCTCTCC | ATGCTGCCCC | ACCTGGCTGA | CCTGGTCAGT | TACAGCATCC | AAAAGGTCAT | 840 |
| TGGCTTTGCT | AAGATGATAC | CAGGATTCAG | AGACCTCACC | TCTGAGGACC | AGATCGTACT | 900 |
| GCTGAAGTCA | AGTGCCATTG | AGGTCATCAT | GTTGCGCTCC | AATGAGTCCT | TCACCATGGA | 960 |
| CGACATGTCC | TGGACCTGTG | GCAACCAAGA | CTACAAGTAC | CGCGTCAGTG | ACGTGACCAA | 1020 |
| AGCCGGACAC | AGCCTGGAGC | TGATTGAGCC | CCTCATCAAG | TTCCAGGTGG | GACTGAAGAA | 1080 |
| GCTGAACTTG | CATGAGGAGG | AGCATGTCCT | GCTCATGGCC | ATCTGCATCG | TCTCCCCAGA | 1140 |
| TCGTCCTGGG | GTGCAGGACG | CCGCGCTGAT | TGAGGCCATC | CAGGACCGCC | TGTCCAACAC | 1200 |
| ACTGCAGACG | TACATCCGCT | GCCGCCACCC | GCCCCGGGC | AGCCACCTGC | TCTATGCCAA | 1260 |
| GATGATCCAG | AAGCTAGCCG | ACCTGCGCAG | CCTCAATGAG | GAGCACTCCA | AGCAGTACCG | 1320 |
| CTGCCTCTCC | TTCCAGCCTG | AGTGCAGCAT | GAAGCTAACG | CCCCTTGTGC | TCGAAGTGTT | 1380 |
| TGGCAATGAG | ATCTCCTGA | | | | | 1399 |

( 2 ) INFORMATION FOR SEQ ID NO:6:

( i ) SEQUENCE CHARACTERISTICS:
        ( A ) LENGTH: 2043 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Rat ( x ) PUBLICATION INFORMATION:
        ( A ) AUTHORS: Burmester, James K.
                Wiese, Russell J.
                Maeda, Nobuyo
                DeLuca, hector F.
        ( B ) TITLE: Structure and regulation of the rat
            1,25- dihydroxyvitamin D3 receptor
        ( C ) JOURNAL: Proc. Natl. Acad. Sci. U.S.A.
        ( D ) VOLUME: 85
        ( F ) PAGES: 9499-9502
        ( G ) DATE: December-1988

( x i ) SEQUENCE DESCRIPTION: SEQ ID NO:6:

| | | | | | | |
|---|---|---|---|---|---|---|
| CGTCCACCGC | CAGACCAGAG | TTCTTTTGGT | CGGACAGATC | TGTGAGACTT | CCAGGAGAGC | 60 |
| ACCCTTGGGC | TCTACTCACC | CTGCTCCTTC | AGGGATGGAG | GCAACAGCGG | CCAGCACCTC | 120 |
| CCTGCCCGAC | CCTGGTGACT | TTGACCGGAA | CGTGCCCCGG | ATCTGTGGAG | TGTGTGGAGA | 180 |
| CCGAGCCACA | GGCTTCCACT | TCAATGCTAT | GACCTGTGAA | GGCTGCAAAG | GTTTCTTCAG | 240 |
| GCGGAGCATG | AAGCGGAAGG | CCCTGTTCAC | CTGTCCCTTC | AATGGAGATT | GCCGCATCAC | 300 |
| CAAGGACAAC | CGGCGACACT | GCCAGGCCTG | CCGGCTCAAA | CGCTGTGTGG | ACATCGGCAT | 360 |
| GATGAAGGAG | TTCATCCTGA | CAGATGAGGA | GGTACAGCGT | AAGAGGGAGA | TGATAATGAA | 420 |
| GAGAAAAGAG | GAAGAGGCCT | TGAAGGACAG | TCTGAGGCCC | AAGCTATCTG | AAGAACAACA | 480 |
| GCACATCATA | GCCATCCTGC | TGGACGCCCA | CCACAAGACC | TATGACCCCA | CCTACGCTGA | 540 |

-continued

```
CTTCAGGGAC  TTCCGGCCTC  CAGTTCGTAT  GGACGGAAGT  ACAGGGAGCT  ATTCTCCAAG     600
GCCCACACTC  AGCTTCTCCG  GGAACTCCTC  CTCCTCCAGC  TCTGACCTGT  ACACCACCTC     660
ACTAGACATG  ATGGAACCAT  CCGGCTTTTC  CAACCTGGAT  CTGAACGGAG  AGGATTCTGA     720
TGACCCGTCT  GTGACTCTGG  ACCTGTCTCC  TCTCTCCATG  CTGCCCCACC  TGGCTGACCT     780
TGTCAGTTAC  AGCATCCAAA  AGGTCATCGG  CTTTGCCAAG  ATGATCCAG   GATTCAGGGA     840
TCTCACCTCC  GATGACCAGA  TTGTCCTGCT  TAAGTCAAGC  GCCATTGAGG  TGATCATGTT     900
ACGCTCCAAC  CAGTCTTTCA  CCATGGATGA  TATGTCCTGG  GACTGTGGCA  GCCAGGACTA     960
CAAGTACGAC  GTCACCGATG  TCTCCAAAGC  TGGGCACACC  CTGGAGCTGA  TCGAGCCCCT    1020
CATAAAGTTC  CAGGTGGGGC  TGAAGAAGCT  GAACTTACAT  GAGGAAGAGC  ATGTCCTTCT    1080
CATGGCCATC  TGCATTGTCT  CCCCGGACCG  ACCTGGGGTC  CAGGACGCCA  AGCTGGTGGA    1140
AGCCATTCAG  GACCGCCTAT  CCAACACGCT  GCAGACCTAC  ATCCGCTGCC  GCCACCCGCC    1200
CCCAGGCAGC  CACCAGCTCT  ATGCCAAGAT  GATCCAGAAA  CTGGCCGACC  TGCGGAGCCT    1260
CAACGAGGAA  CACTCCAAAC  AATACCGCTC  CCTCTCCTTC  CAGCCCGAGA  ATAGCATGAA    1320
GCTCACACCC  CTTGTGCTGG  AGGTGTTCGG  CAATGAGATC  TCCTGACCAG  GGTGGCCCAC    1380
AGTGGTGCCT  GGGTAGGGCC  GCTCCTCCAG  AGCCCTGTGC  CCAGGCCCTG  GGCTTGGTTG    1440
CAGCCCAGCA  GTGCCTCCTG  CCCTTTCTGG  AGTTCAGTCC  TTCCTCTGCC  ATGGCCTCTG    1500
TCTGTCTGCC  TCATCCTTTC  TCCTGCCCAG  CCTAACACCT  GGTCTCCCTT  TCCTGTAGAC    1560
CTCGAGTTGC  TCCTGTCTCT  TGAGACCTCA  GTTAGGAGAG  GCTGCTGTTT  ATCTGACAAA    1620
GGAACTCAAT  TGGGGATAGA  GGGCAGGGGC  TGAAGGCGGA  ACTCTGCCTA  GGGGATGCCT    1680
CCACCACAAG  GGGCTGCTGC  TTGTGTCAAG  GGAGGCAGGC  AGAAGAGACG  CATTCACTCC    1740
TCAGGGACAG  GTACCTGCAC  CTCCCCTCAC  TCCAGCCCTA  CCTGCCCAAA  GCCTAGTGAG    1800
AAATCTGGCC  CCTGCCTGCG  AAGGGTACAC  AACCTACCCA  TCATCCCTAC  TGTGTCCCGT    1860
CTCGTCCTGC  CGCCTGTCTG  TGTTATTCTG  ACCCGGGGGA  GTAGGTCACT  GAGGGGCCTC    1920
CTTCCTCTGC  CTTTATACTC  ACGGGGCTCA  CTCACTGCCA  AGATGACCAA  ATACACTACC    1980
ACACGAACCA  AGGAGCACTC  ACCCAGCCCT  GCAGTTCCCA  CCTTTGAGGT  TTTGCCATGG    2040
GAA                                                                      2043
```